(12) United States Patent
Emans et al.

(10) Patent No.: US 6,464,711 B1
(45) Date of Patent: Oct. 15, 2002

(54) ARTICULATING MECHANISM FOR STEERABLE SURGICAL CUTTING INSTRUMENTS

(75) Inventors: Matthew Emans, Boston, MA (US); Christopher Zirps, Milton, MA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/527,256

(22) Filed: Mar. 17, 2000

Related U.S. Application Data (60) Provisional application No. 60/125,452, filed on Mar. 19, 1999.

(51) Int. Cl.$^7$ .................................................. A61B 17/32
(52) U.S. Cl. ..................................................... 606/167
(58) Field of Search .......................... 606/1, 159, 170, 606/171, 174, 180; 604/22; 600/562–568, 101, 139, 141, 142, 146, 147, 149, 150

(56) References Cited

U.S. PATENT DOCUMENTS

| | | | |
|---|---|---|---|
| 4,499,895 A | * | 2/1985 | Takayama |
| 4,646,738 A | * | 3/1987 | Trott |
| 5,084,052 A | * | 1/1992 | Jacobs .......................... 606/170 |
| 5,285,795 A | * | 2/1994 | Ryan et al. .................. 600/568 |
| 5,454,827 A | | 10/1995 | Aust et al. |
| 5,522,788 A | * | 6/1996 | Kuzmak ...................... 600/141 |
| 5,540,706 A | | 7/1996 | Aust et al. |
| 5,618,294 A | | 4/1997 | Aust et al. |
| 5,669,926 A | | 9/1997 | Aust et al. |
| 5,885,288 A | | 3/1999 | Aust et al. |
| 5,899,914 A | | 5/1999 | Zirps et al. |
| 5,938,678 A | | 8/1999 | Zirps et al. |

FOREIGN PATENT DOCUMENTS

| EP | 0 623 317 A1 | * 11/1994 |
|---|---|---|
| WO | WO 93/00048 | * 1/1993 |

* cited by examiner

*Primary Examiner*—Kevin Shaver
*Assistant Examiner*—Scott Szmal (57) ABSTRACT

A steerable surgical cutting instrument incorporating an articulating mechanism comprises a bendable outer tubular member, a bendable inner member disposed in the outer tubular member, at least one actuating wire extending from the outer tubular member to effect bending of the outer and inner members when the actuating wire is pulled proximally, an outer hub secured to a proximal end of the outer tubular member and an inner hub secured to a proximal end of the inner member proximally of the outer hub. The outer and inner hubs are releasably connectible to a powered surgical handpiece used to rotate the inner member within the outer member to cut anatomical tissue at a distal end of the instrument. The articulating mechanism includes the outer hub, a wire guide disposed on the outer member distally of the outer hub, an actuator pivotably mounted on the outer hub and a housing assembled on the outer hub distally of the powered surgical handpiece. The wire guide guides the actuating wire to extend proximally from the wire guide for attachment to the actuator, which is pivotable to pull the actuating wire proximally to effect bending of the outer and inner members.

33 Claims, 7 Drawing Sheets

ARTICULATING MECHANISM FOR STEERABLE SURGICAL CUTTING INSTRUMENTS

CROSS-REFERENCE TO RELATED PATENT APPLICATIONS

This application claims priority from prior provisional patent application Ser. No. 60/125,452 filed Mar. 19, 1999, the disclosure of which is incorporated herein by reference.

BACKGROUND OF THE INVENTION

1. Field of the Invention

The present invention relates to steerable surgical cutting instruments and, more particularly, to articulating mechanisms for steerable surgical cutting instruments powered by powered surgical handpieces to cut anatomical tissue.

2. Brief Discussion of the Related Art

A typical surgical cutting instrument powered by a powered surgical handpiece includes elongate inner and outer members having inner and outer hubs, respectively, releasably coupled with the powered surgical handpiece. The handpiece typically rotates the inner member relative to the outer member to effect cutting of anatomical tissue at a distal end of the instrument. Cutting of the anatomical tissue is typically accomplished with a distal end of the inner member, which is exposed from an open distal end of the outer member. In order to better access anatomical tissue to be cut, it is desirable in many circumstances for the outer and inner members to be bendable or steerable to selectively adjust the position of the instrument distal end.

Bending or steering of outer and inner members of a surgical cutting instrument has been accomplished with the use of wires or cables as represented by U.S. Pat. No. 5,938,678 to Zirps et al, U.S. Pat. No. 5,899,914 to Zirps et al, U.S. Pat. No. 5,885,288 to Aust et al, U.S. Pat. No. 5,669,926 to Aust et al, U.S. Pat. No. 5,618,294 to Aust et al, U.S. Pat. No. 5,540,706 to Aust et al, and U.S. Pat. No. 5,454,827 to Aust et al.

In the area of steerable surgical cutting instruments and, in particular, steerable shavers, powered by powered surgical handpieces, there are unfulfilled needs. A need exists for an articulating mechanism that guides the wires used to impart bending to the outer and inner members, facilitates movement of the wires to effect bending and release of the outer and inner members, and resists kinking of the wires during actuation and release. There is a further need for an articulating mechanism including an outer hub that allows for mounting of a wire guide and a pivotable actuator used to move the actuating wires. Also, there is a need for an outer hub providing guidance for the wires, limits on pivotal movement of the actuator and/or proper positioning of the wire guide. A need further exists for an articulating mechanism including housing sections forming a housing that shields the working parts of the articulating mechanism, facilitates proper assembly and cooperates with the actuator to lock the actuator in a pivoted position.

SUMMARY OF THE INVENTION

Accordingly, it is a primary object of the present invention to fulfill unmet needs in the field of steerable surgical cutting instruments powered by powered surgical handpieces.

Another object of the present invention is to provide an articulating mechanism for a steerable shaver powered by a powered surgical handpiece.

A further object of the present invention is to pivotably mount an actuator on an outer hub of a steerable surgical cutting instrument for effecting movement of actuating wires to bend outer and inner members of the instrument in response to pivotable movement of the actuator, with the actuator being mounted distally of a powered surgical handpiece to which the outer hub is releasably connectible.

An additional object of the present invention is to guide the wires of a steerable surgical cutting instrument, for attachment to a pivotable actuator, via a wire guide disposed on an outer member of the instrument distally of an outer hub secured to a proximal end of the outer member.

The present invention also has as an object to facilitate assembly of an articulating mechanism for a steerable surgical cutting instrument.

It is a further object of the present invention to shield the working parts of an articulating mechanism for a steerable suction cutting instrument with a housing formed of housing sections assembled over an outer hub of the instrument distally of a powered surgical handpiece used to power the instrument to cut anatomical tissue.

Some of the advantages of the present invention are that the outer hub has structure for mounting the wire guide thereto, the wire guide guides actuating and return wires of the instrument, structure on the outer hub guides the return wires from the wire guide for attachment to the actuator, pivotal movement of the actuator is limited or controlled via structure on the outer hub, the outer hub has a port for irrigation through the instrument, the wire guide has an inner surface configured to guide the wires and keep them from kinking during actuation and release, the wire guide locks onto the outer hub to maintain proper location, movement of the wires is eased, attachment of the wires to the actuator is facilitated by structure of the actuator, the pivot point for the actuator provides the necessary travel for the wires, a locking member on the actuator is lockingly engageable with a plurality of detents on the housing to lock the actuator in a selected one of a plurality of pivoted positions, the locking member can be removed if locking is not desired, the locking member is capable of being easily released from the detents to effect release of the outer and inner members of the instrument, the housing covers the working parts of the articulating mechanism for safety, the housing sections can be ultrasonically welded to insure durability, and the housing sections are provided with locating features to facilitate assembly.

These and other objects, advantages and benefits are achieved with the present invention as generally characterized in an articulating mechanism incorporated in a steerable surgical cutting instrument, such as a steerable shaver, powered by a steerable surgical handpiece. A steerable surgical cutting instrument including the articulating mechanism of the present invention comprises a bendable outer tubular member having open distal and proximal ends, a bendable inner member disposed in the outer tubular member and having a distal end exposed from the distal end of the outer tubular member and having a proximal end, at least one actuating wire extending proximally from the outer tubular member to effect bending of the outer and inner members when the actuating wire is pulled in a proximal direction, an outer hub secured to the proximal end of the outer tubular member and an inner hub secured to the proximal end of the inner member. The outer hub has a passage therethrough receiving the inner member with the inner hub disposed proximally of the outer hub. The outer and inner hubs are releasably connectible to a powered surgical handpiece used to rotate the inner member within the outer tubular member to cut anatomical tissue with the distal end of the inner member. In a preferred embodiment, a pair of actuating wires extend proximally from one side of the outer tubular member and a pair of return wires extend proximally from an opposite side of the outer tubular member. The return wires effect straightening of the outer and inner members when the actuating wires are not pulled proximally. The articulating mechanism includes the outer hub, a wire guide disposed on the outer tubular member, an actuator to which the actuating and return wires are attached and a housing mounted on the outer hub distally of the powered surgical handpiece. The actuator is pivotally mounted on the outer hub and has a rest position wherein the outer and inner members are straight. The actuator is pivotably or rotatably movable from the rest position to a pivoted position to pull the actuating wires proximally to effect bending of the outer and inner members. The wire guide has a lumen through which the outer tubular member passes, and an inner surface of the wire guide is configured to guide the actuating and return wires to extend proximally from the wire guide for attachment to the actuator. The wire guide is assembled to engagement members on the outer hub and is held and located by structure on the housing. The outer hub has travel stops cooperating with the actuator to limit or control pivotable or rotational movement of the actuator. The outer hub has guide structure thereon guiding the return wires extending from the wire guide for attachment to the actuator. The housing has detents cooperating with a locking member on the actuator to releasably lock the actuator in various pivoted positions. The outer hub includes an irrigation port for the instrument by which an irrigating fluid can be introduced between the inner and outer members.

Inasmuch as the present invention is subject to many variations, modifications and changes in detail, it is intended that all subject matter discussed above or shown in the accompanying drawings be interpreted as illustrative only and not be taken in a limiting sense.

DESCRIPTION OF THE PREFERRED EMBODIMENTS

The articulating mechanism according to the present invention can be used with or incorporated in any steerable suction cutting instrument having an inner blade member with a flexible or bendable portion movably disposed within an outer member with a flexible or bendable portion and one or more actuating wires which are secured to the outer blade member to cause the instrument to bend when pulled. An example of such an instrument is described in U.S. Pat. No. 5,669,926, the disclosure of which is incorporated herein by reference.

Figure 1:
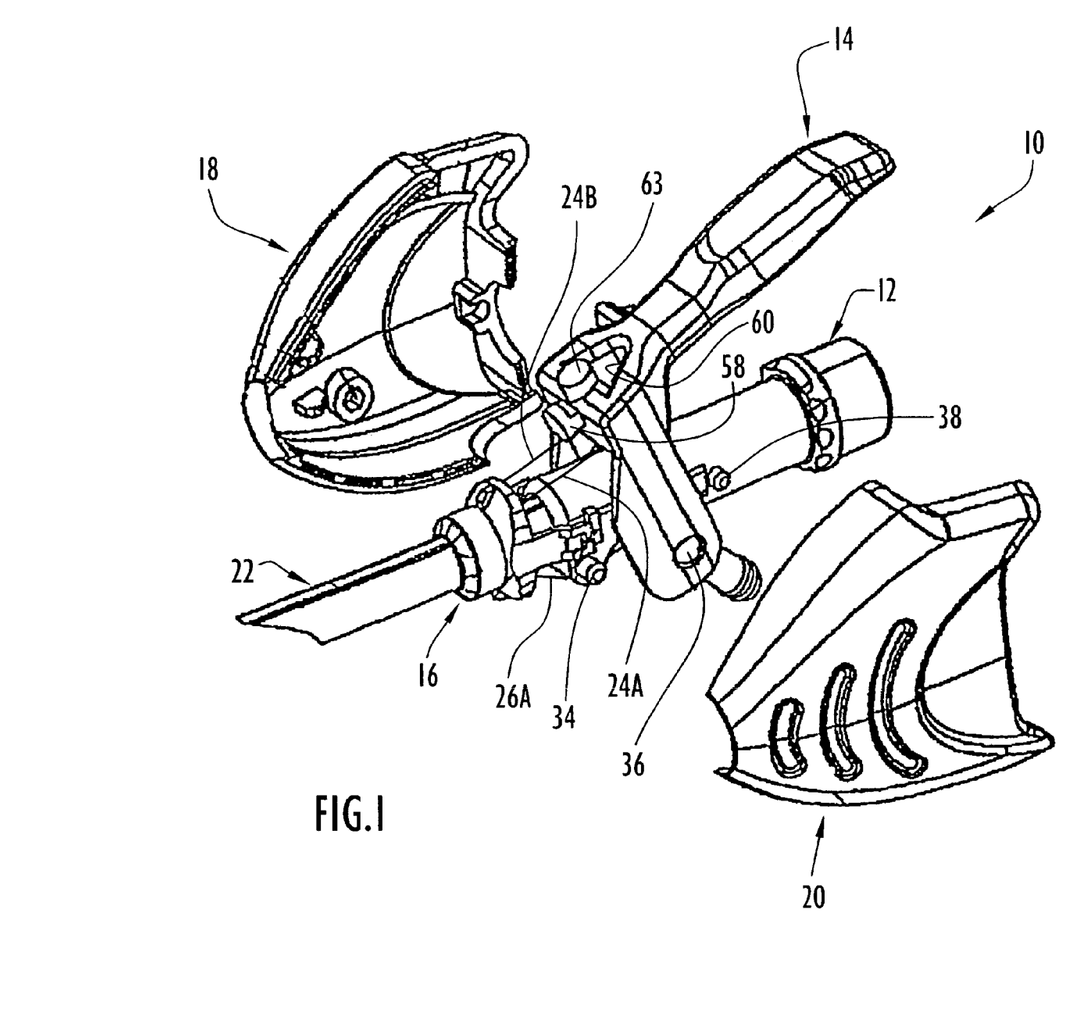
FIG. 1 is a broken perspective view of an articulating mechanism according to the present invention.

An articulating mechanism for a steerable suction cutting instrument and, in particular, a steerable shaver, according to the present invention is illustrated in perspective in FIG. 1 at 10. Articulating mechanism 10 includes an outer hub 12, a lever or actuator 14 pivotably mounted on the outer hub, a wire guide 16, and a pair of clam shell housing sections 18 and 20 positioned on opposite sides of the outer hub to form an exterior cover or housing for moving parts of the mechanism. An outer member 22 of a steerable suction cutting instrument extends distally from outer hub 12 with a pair of actuating wires or wire ends 24A and 24B extending from one side of the outer member to lever 14 via wire guide 16 and a pair of return wires or wire ends 26A and 26B extending from an opposite side of the outer member to the lever via the wire guide. In the case of articulating mechanism 10, the actuating wires 24A and 24B extend from an upper side of the outer member, and the return wires 26A and 26B extend from a lower side of the outer member, looking proximally in FIG. 1. The actuating wires are spaced from one another so that the actuating wire 24A may be considered a right actuating wire, and the actuating wire 24B may be considered a left actuating wire, looking proximally in FIG. 1. The return wires are similarly spaced from one another so that the return wire 26A may be considered a right return wire, and the return wire 26B may be considered a left return wire, the return wire 26B not being visible in FIG. 1.

Figures 2, 6:
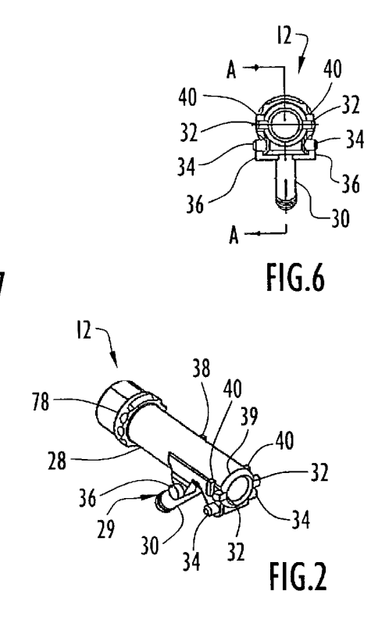
FIG. 2 is a front perspective view of an outer hub for the articulating mechanism.
FIG. 6 is a proximal end view of the outer hub.
Figure 3:
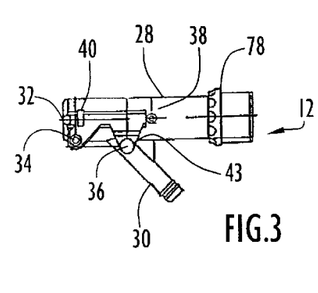
FIG. 3 is a right side view of the outer hub.
Figure 4:
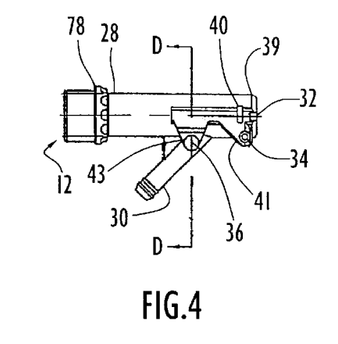
FIG. 4 is a left side view of the outer hub.
Figure 5:
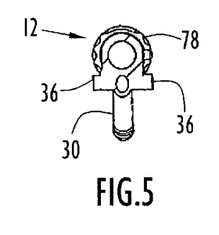
FIG. 5 is a cross-sectional view of the outer hub taken along line D—D in FIG. 4.
Figure 7:
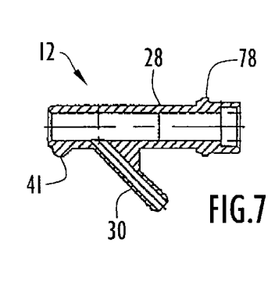
FIG. 7 is a cross-sectional view of the outer hub taken along line A—A in FIG. 6.
Figure 8:
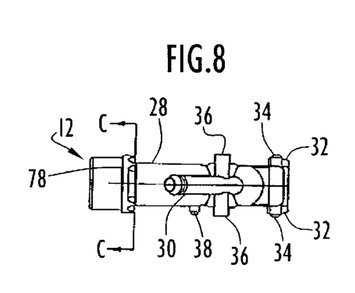
FIG. 8 is a bottom view of the outer hub.
Figure 9:
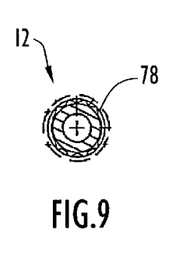
FIG. 9 is a cross-sectional view of the outer hub taken along line C—C in FIG. 8.
Figure 10:
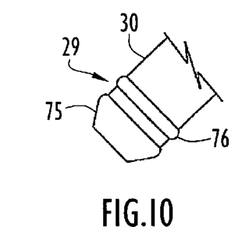
FIG. 10 is an enlarged fragmentary view of a coupling for an irrigation port of the outer hub.

FIG. 2 is a front perspective view of the outer hub. FIGS. 3 and 4 are right and left side views of the outer hub, respectively. FIG. 5 is a cross-sectional view of the outer hub taken through line D—D in FIG. 4. FIG. 6 is an end view of the outer hub looking proximally. FIG. 7 is a cross-sectional view of the outer hub taken through line A—A in FIG. 6. FIG. 8 is a bottom view of the outer hub. FIG. 9 is a cross-sectional view of the outer hub taken through line C—C in FIG. 8. FIG. 10 is an enlarged fragmentary view of the coupling at the proximal end of the outer hub irrigation port.

As can be seen from FIGS. 2–9, outer hub 12 is similar to the outer hub in a conventional surgical cutting instrument such as a conventional shaver blade. Like a conventional outer hub, the outer hub 12 includes a tubular body 28 having a lumen or passage therethrough, and an irrigation port 30 extending proximally from a lower side of the tubular body 28 at an acute angle to terminate at a coupling 29. The irrigation port 30 is tubular or hollow, and thusly has an irrigation passage therethrough communicating with the lumen of the tubular body 28. The coupling 29, as shown in FIG. 10, has a tapered nose 75 and a rounded annular flange 76 spaced from nose 75 to form structure facilitating removable connection or coupling of the irrigation port with one end of a length of conventional irrigation tubing. A proximal length portion of the tubular body 28 is of increased diameter and terminates distally at an annular flange 78 provided with recesses for engaging one or more detents or locking members of a powered surgical handpiece so as to couple the hub 12 with the handpiece as explained further below. The outer hub 12 is secured to a proximal end of the outer member 22, which is tubular to receive the inner blade member of the steerable cutting instrument. The inner blade member passes through the lumen of the outer hub 12 and has a proximal end secured to an inner hub, which is disposed proximally of the outer hub 12 for releasable connection to the powered surgical handpiece.

In accordance with the present invention, the outer hub 12 includes a pair of detents or engagement members 32 at a distal end thereof for mating with wire guide 16, a pair of guide posts 34 for guiding the return wires 26A and 26B, respectively, and a pair of pivot pins 36 upon which the lever 14 is pivotally mounted. The hub also includes at least one first travel stop 38 located proximally of the pivot pins 36 to limit pivotal movement of the lever in a first direction, i.e. toward the hub 12, and a pair of second travel stops 40 between the pivot pins 36 and the guide posts 34 to limit pivotal movement of the lever in a second direction, i.e. away from the hub 12. The distal end of tubular body 28 is beveled, tapered or angled between a circumferential junction 39 and a distal circumferential edge. The distal end of tubular body 28 has a distal extension 41 extending downwardly from a lower side thereof and extending transversely between left and right sides of tubular body 28. A proximal extension 43 extends downwardly from the lower side of the tubular body 28 and extends transversely between the left and right sides thereof. The proximal extension 43 is bisected by an upper end of the irrigation port 30.

The detents 32 are located at 1800 spaced locations on the left and right sides of the tubular body 28 along or adjacent the distal circumferential edge, such locations being disposed in a horizontal plane bisecting the hub 12 horizontally and containing a central longitudinal axis of hub 12. Each detent 32 has distal, proximal, upper and lower sides extending laterally outwardly from the tubular body 28 to an end surface that is angled outwardly in a proximal direction relative to the tubular body 28.

The guide posts 34 are cylindrical in configuration and extend laterally outwardly from the distal extension 41 to rounded ends. The guide posts 34 are disposed at lower left and lower right sides, respectively, of tubular body 28 and are coaxially aligned. A central longitudinal axis of the guide posts 34 is perpendicular to the central longitudinal axis of the hub 12. The central longitudinal axis of the guide post 34 is disposed a small distance outwardly of the external circumference of tubular body 28 and a small distance proximally of the detents 32.

The pivot pins 36 are cylindrical in configuration and extend laterally outwardly from the proximal extension 43 to flat or planar end surfaces. The pivot pins 36 are disposed at the lower left and lower right sides, respectively, of tubular body 28 and are coaxially aligned. A central longitudinal axis of the pivot pins 36 is parallel to the central longitudinal axis of guide posts 34. The central longitudinal axis of the pivot pins 36 is disposed a distance outwardly of the external circumference of tubular body 28 that is greater than the distance that the central longitudinal axis of the guide posts 34 is disposed outwardly of the external circumference. The central longitudinal axis of pivot pins 36 is disposed proximally of the central longitudinal axis of guide posts 34 and intersects an upper end of irrigation port 30. Arcuate segments of the cylindrical outer surfaces of the pivot pins 36 form part of the outer surface of the proximal extension 43.

The first travel stop 38 is cylindrical in configuration and protrudes laterally outwardly from the tubular body 28 on one of the left or right sides thereof, the travel stop 38 being disposed on the right side of the tubular body as shown in FIGS. 2 and 3. The travel stop 38 is in longitudinal alignment with the detent 32 located on the right side of tubular body 28. The travel stop 38 is disposed proximally of the pivot pin 36 located on the lower right side of the tubular body, but is closer to such pivot pin 36 than to the flange 78.

The second travel stops 40 are rectangular in configuration and protrude laterally outwardly from the left and right sides, respectively, of tubular body 28, the travel stop 40 on the right side of tubular body 28 being in line with the travel stop 38. The travel stops 40 are aligned with one another on the left and rights sides of the tubular body, and have a length extending in a vertical direction. Each travel stop 40 has long distal and proximal parallel side walls and short upper and lower parallel side walls extending laterally outwardly from the tubular body 28 to a flat end surface. The distal side walls of the travel stops 40 are spaced proximally from the proximal sides of the detents 32. Centers of the travel stops 40 are offset slightly in the vertical direction from centers of the detents 32, respectively.

Figure 11:
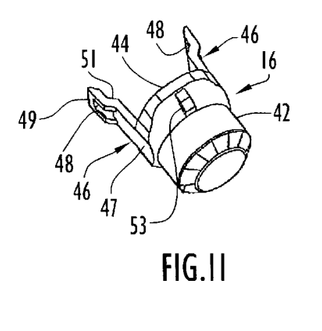
FIG. 11 is a front perspective view of a wire guide for the articulating mechanism.
Figure 12:
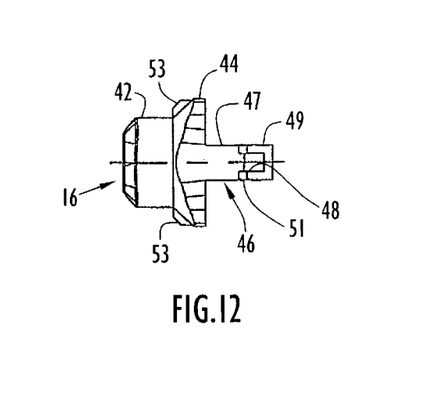
FIG. 12 is a right side view of the wire guide.
Figure 13:
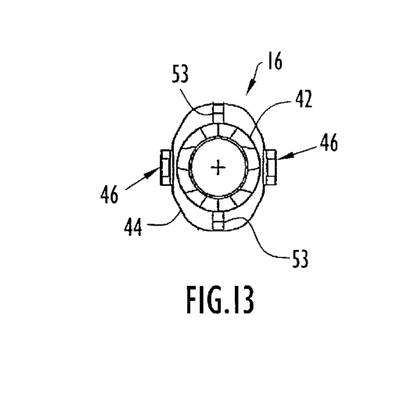
FIG. 13 is a front view of the wire guide.
Figure 14:
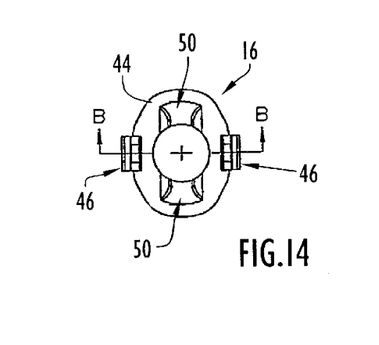
FIG. 14 is a rear view of the wire guide.
Figure 15:
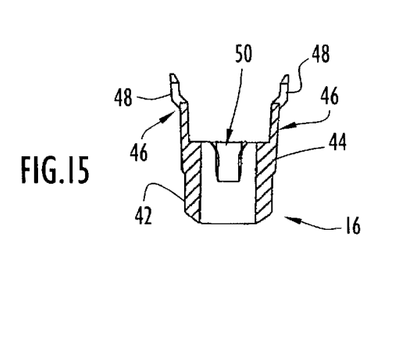
FIG. 15 is a cross-sectional view of the wire guide taken along line B—B in FIG. 14.
Figure 16:
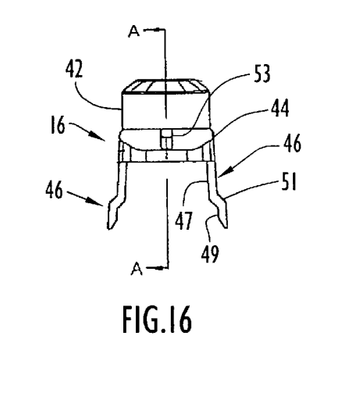
FIG. 16 is a bottom view of the wire guide.
Figure 17:
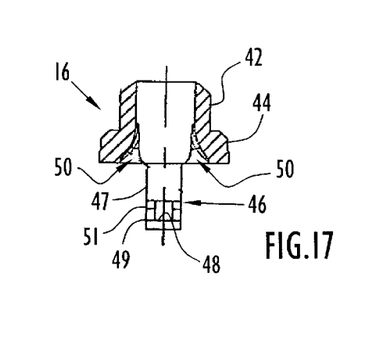
FIG. 17 is a cross-sectional view of the wire guide taken along line A—A in FIG. 16.

FIG. 11 is a front perspective view of the wire guide. FIG. 12 is a right side view of the wire guide. FIG. 13 is a front view of the wire guide. FIG. 14 is a rear view of the wire guide. FIG. 15 is a cross-sectional view of the wire guide taken through line B—B in FIG. 14. FIG. 16 is a bottom view of the wire guide. FIG. 17 is a cross-sectional view of the wire guide taken through line A—A in FIG. 16.

As shown in FIGS. 11–17, wire guide 16 includes a hollow, cylindrical body 42 with an outwardly extending flange 44 proximally joined to cylindrical body 42 and a pair of arms 46 which extend proximally from the flange 44 to ends having openings 48 which receive detents 32 on the left and right sides of the tubular body 28 to lock the wire guide in a proper location relative to the outer hub 12. A lumen or passage extends through the cylindrical body 42 and the flange 44 for receiving the outer member 22 therethrough. The inner diameter of the wire guide is configured or sized to fit telescopically around the outer member, and a pair of slots 50 are formed at diametrically opposed locations on the interior of the wire guide to receive the actuating wires and the return wires, respectively. The wires extend through the lumen of the wire guide, and the slots 50, which communicate with the lumen of the wire guide, hold the wires in place and keep them from kinking during actuation and release as described further below. The arms 46 have distal segments 47 merging with flat external surfaces or sides of flange 44, proximal segments 49 laterally offset from distal segments 47 and intermediate segments 51 extending angularly between the distal and proximal segments. The distal segments 47 are angled slightly outwardly in the proximal direction relative to a central longitudinal axis of wire guide 16. The intermediate segments 51 are angled outwardly in the proximal direction from the distal segments 47 such that the proximal segments 49 are offset laterally outwardly from the distal segments. Each opening 48 is formed partly in the intermediate segment and partly in the distal segment of the corresponding arm 46 and is configured to receive a detent 32, such as with a friction or snap fit. Each arm 46 has a terminal end segment between its opening 48 and a proximal most edge. Raised nubs 53 are provided on the front of flange 44. The nubs 53 are offset about 90° from the arms 46 and are spaced about 180° from one another.

The wire guide 16 is disposed on the outer member with the outer member extending through the lumen of the wire guide, which is disposed distally of the outer hub 12, and the arms 46 extending toward the outer hub on the left and right sides of tubular body 28. The wire guide is assembled to the hub 12 by positioning detents 32 in the openings 48 with the angled intermediate segments 51 and the offset proximal segments 49 of the arms 46 accommodating the external circumferential or diametric dimension of the tubular body 28. The flange 44 is spaced distally from the distal circumferential edge of the tubular body, and the terminal end segments of the arms are accommodated or received between the proximal sides of detents 32 and the distal side walls of travel stops 40. In the assembled condition, one of the slots 50 of the wire guide is disposed at the upper side of the outer member 22, and the other of the slots 50 is disposed at the lower side of the outer member 22. The upper slot 50 extends laterally or arcuately on the interior of wire guide 16 a sufficient distance to accommodate the actuating wires 24A and 24B therein. The lower slot 50 extends laterally or arcuately on the interior of the wire guide a sufficient distance to accommodate the return wires 26A and 26B therein. The slots 50 have a lateral dimension or width that flares outwardly or increases at a proximal end of flange 44 where the wires exit the flange 44 and extend proximally for attachment to lever 14. The nubs 53 are disposed in alignment with the upper and lower sides, respectively, of the tubular body 28.

Figure 18:
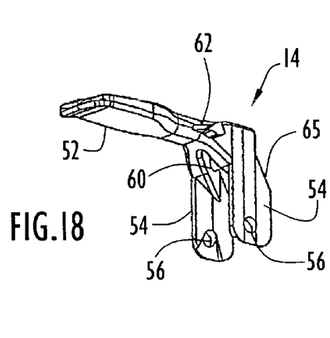
FIG. 18 is a rear perspective view of an actuator for the articulating mechanism.
Figure 19:
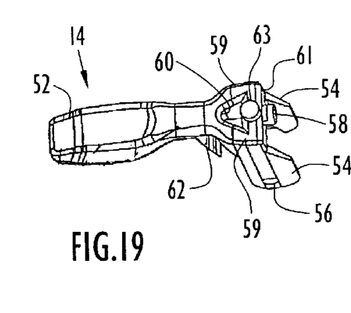
FIG. 19 is a top perspective view of the actuator.
Figure 20:
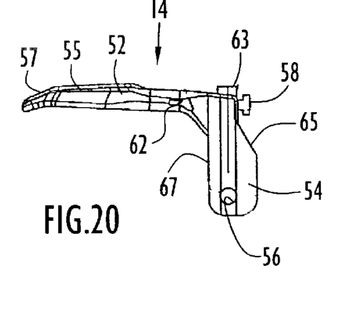
FIG. 20 is a left side view of the actuator.
Figure 21:
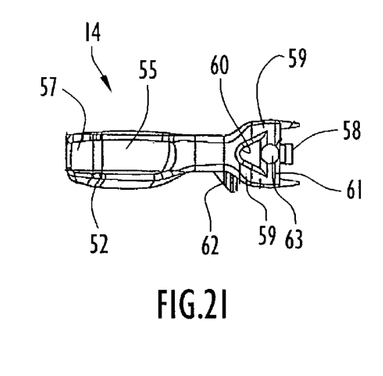
FIG. 21 is a top view of the actuator.
Figure 22:
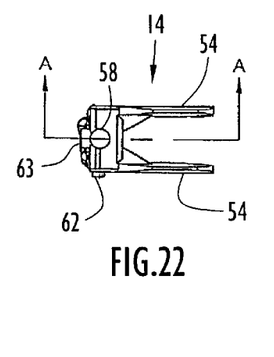
FIG. 22 is a front view of the actuator.
Figure 23:
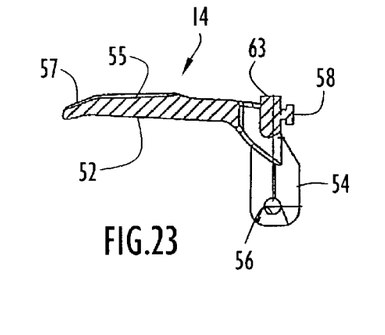
FIG. 23 is a cross-sectional view of the actuator taken along line A—A in FIG. 22.

FIG. 18 is a rear perspective view of the lever or actuator. FIG. 19 is a top perspective view of the lever. FIG. 20 is a side view of the lever. FIG. 21 is a top view of the lever. FIG. 22 is a front view of the lever. FIG. 23 is a cross-sectional view of the lever taken through line A—A in FIG. 22.

As shown in FIGS. 18–22, lever 14 includes an elongate handle 52 with proximal and distal ends, and a pair of pivot plates 54 extending downwardly from the distal end of the handle. Pivot plates 54 are parallel and have openings or holes 56 formed in lower ends thereof in opposed relation to receive pivot pins 36 on the outer hub to pivotally or rotatably mount the lever on the outer hub. The handle 52 includes a rearward section joined to a forward section by a neck. The rearward section is asymmetrical about a central longitudinal axis of handle 52 with one side thereof extending laterally a greater distance than the other side thereof as best shown in FIGS. 19 and 21, which show the left side of the rearward section extending laterally a greater distance than the right side thereof. The rearward section has a distal upper surface segment 55 and a proximal upper surface segment 57 angled downwardly from the distal upper surface segment. The distal and proximal upper surface segments 55 and 57 have a concave configuration to facilitate engagement of handle 52 by the pad of a thumb or forefinger used to depress the lever 14 to pull the actuating wires proximally.

The forward section of handle 52 includes a pair of legs 59 angled outwardly from the neck and a crosspiece 61 extending between and connecting distal ends of legs 59. A knob or retention member 58 projects from the distal end of the handle, the knob 58 projecting distally or forwardly from the front center of crosspiece 61. An opening 60 is formed through the handle adjacent the knob 58 to provide a passage through which the actuating and return wires can be upwardly passed before being tied, wrapped around or otherwise attached to the knob 58, the opening 60 being circumscribed by legs 59 and crosspiece 61. A button 63 protrudes upwardly from the top center of crosspiece 61 allowing the left actuating and return wires to be disposed on a left side of button 63 and the right actuating and return wires to be disposed on a right side of button 63 after the wires exit the opening 60 for attachment to knob 58. The pivot plates 54 extend in a perpendicular or substantially perpendicular direction from the distal end of handle 52. Each pivot plate 54 has a forward edge defining an angled forward abutment 65 and has a rearward edge defining a straight rearward abutment 67. When the lever 14 is assembled to hub 12 with the pivot pins 36 disposed in the holes 56, respectively, the pivot plates 54 straddle the tubular body 28 and are disposed along the left and right sides, respectively, thereof. The forward abutments 65 are adapted to engage or abut the proximal walls of travel stops 40, respectively, to limit pivotal or rotational movement of lever 14 away from hub 12, i.e. in a counterclockwise direction around pivot pins 36 looking at FIG. 1. The rearward abutment 67 disposed on the left side of tubular body 28 is adapted to engage or abut the travel stop 38 to limit pivotal or rotational movement of the lever toward the hub, i.e. in a clockwise direction around pivot pins 36 looking at FIG. 1.

A removable locking member or finger 62 projects from a longitudinal or lateral edge of the handle 52 between the proximal and distal ends thereof to engage one-way detents or ribs on one of the housing sections to provide passive position locking or indexing for flexure angle increase and active release for flexure angle decrease as explained further below. Release of the locking member 62 is assisted by the use of offset holes and a flexible material. The locking member 62 can be clipped off if locking is not desired. In the case of lever 14, the locking finger 62 extends from the left side of handle 52 at the junction of the neck with the corresponding leg 59. The locking finger 62 has a forward edge extending from the lateral or longitudinal left side edge of the handle in a perpendicular or substantially perpendicular direction to lock behind the detents or ribs, which are formed in the left housing section, as the lever is rotated toward the hub. Locking finger 62 has a rearward edge forming an acute angle with the forward edge so as to facilitate movement of the locking finger 62 past the detents or ribs. The position of the holes 56 relative to the wire attachment is such that the desired travel of the wires is achieved. Moreover, the mechanical advantage achieved with the above arrangement allows easier movement of the wires.

Figures 24, 25, 29, 30, 31:
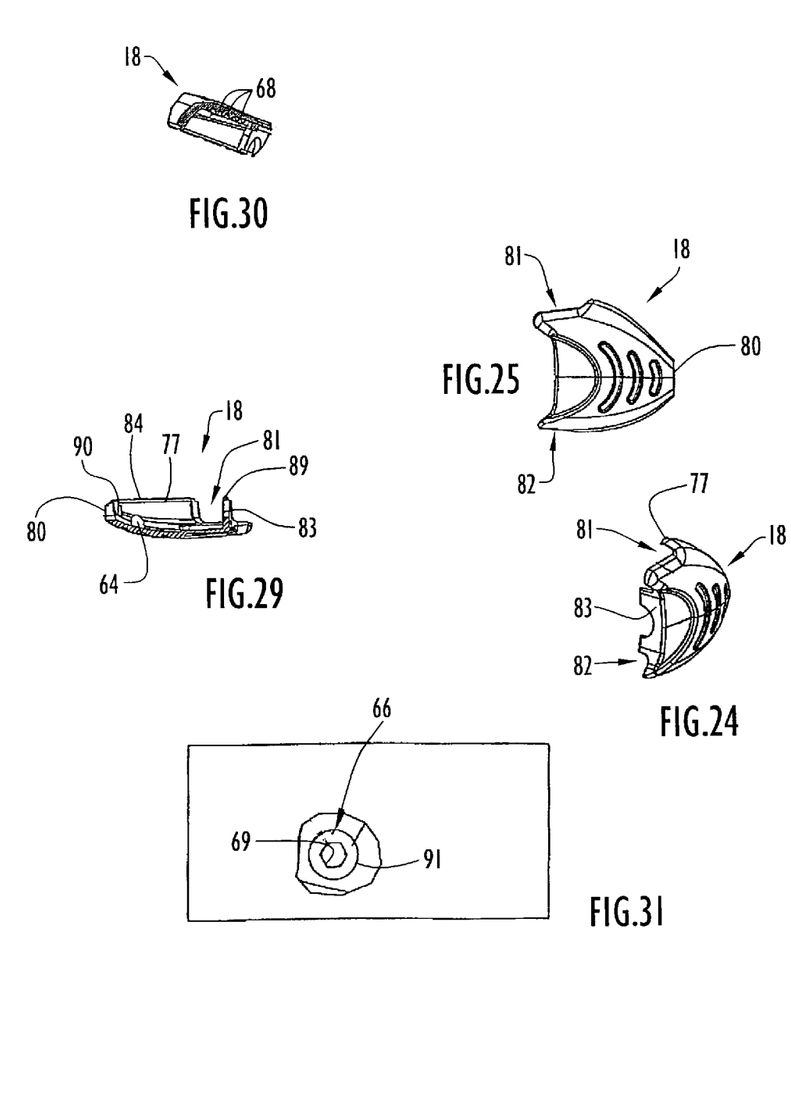
FIG. 24 is a rear perspective view of a left housing section of a housing for the articulating mechanism.
FIG. 25 is an exterior side view of the left housing section.
FIG. 29 is a cross-sectional view of the left housing section taken along line A—A in FIG. 28.
FIG. 30 is a cross-sectional view of the left housing section taken along line B—B in FIG. 28.
FIG. 31 is an enlarged fragmentary view of the interior of the left housing section.
Figure 26:
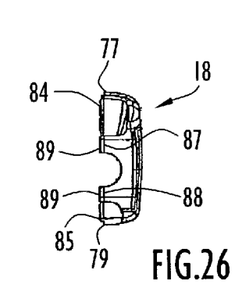
FIG. 26 is a rear view of the left housing section.
Figure 27:
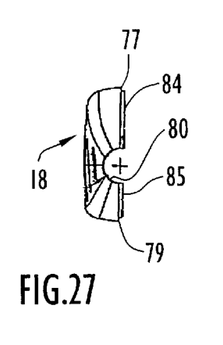
FIG. 27 is a front view of the left housing section.
Figure 28:
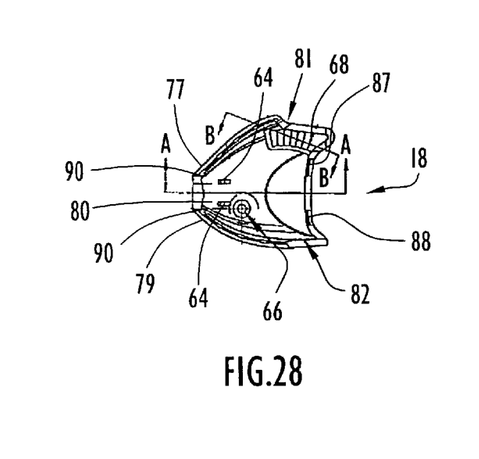
FIG. 28 is an interior side view of the left housing section.

FIG. 24 is a rear perspective view of the left housing section. FIG. 25 is an exterior side view of the left housing section. FIG. 26 is a rear view of the left housing section. FIG. 27 is a front view of the left housing section. FIG. 28 is an interior side view of the left housing section. FIG. 29 is a cross-sectional view of the left housing section taken through line A—A in FIG. 28. FIG. 30 is a cross-sectional view of the left housing section taken through line B—B in FIG. 28. FIG. 31 is an enlarged fragmentary view of the interior of the left housing section illustrating the hexagonal hole fixture in detail.

As shown in FIGS. 24–31, left housing section 18 is a hollow shell with locating members or features 64 for locating the wire guide 16, a hexagonal hole fixture 66 for receiving the guide post 34 at the lower left side of the tubular body 28, and one-way detents or ribs 68 which function as a locking mechanism in combination with the locking finger 62 on the lever. The left housing section 18 has upper and lower edges 77 and 79, respectively, extending proximally from a distal edge 80 to upper and lower cut-outs or notches 81 and 82, respectively. The upper notch 81 extends proximally from the upper edge 77 to an inwardly angled end wall 83. The lower notch 82 extends proximally from the lower edge 79 to the end wall 83. Upper and lower protruding rims 84 and 85 having indentations therein extend along the upper and lower edges 77 and 79, respectively. The distal edge 80 is partial circular or semi-circular with a diametric or circumferential dimension corresponding to the external diameter or circumference of the cylindrical body 42 of wire guide 16. The upper notch 81 cooperates with a corresponding upper notch in the right housing section to allow the handle 52 to protrude through the housing formed by the left and right housing sections when they are assembled on hub 12 and is of sufficient length between upper edge 77 and the end wall 83 to accommodate a desired range of rotational or pivotal movement of handle 52. The lower notch 82 cooperates with a corresponding lower notch in the right housing section to allow the irrigation port 30 to pass through the housing formed when the left and right housing section are assembled to hub 12. The end wall 83 has a partial circular or semi-circular recess therein with a diametric or circumferential dimension corresponding to the external diameter or circumference of the tubular body 28. The end wall 83 has upper and lower edge segments 87 and 88 extending upwardly and downwardly, respectively, from the recess. The upper and lower edge segments of end wall 83 have protruding rims 89 thereon, respectively. Protuberances 90 are disposed on the inner or interior surface of the left housing section adjacent distal ends of the upper and lower protruding rims 84 and 85, respectively.

The locating members 64 are elongate protrusions disposed on the inner surface of the left housing section 18 proximally of the protuberances 90. The locating members 64 are spaced from each other in the vertical direction so as to define an upper locating member disposed above a central longitudinal axis of the left housing section and a lower locating member disposed below the central longitudinal axis of the left housing section. The locating members 64 extend parallel to one another and are in longitudinal alignment with the distal edge 80. When the left housing section 18 is assembled to hub 12 after the hub 12 has been assembled to the wire guide 16, the flange 44 of the wire guide is held between the protuberances 90 and forward surfaces or walls of the locating members 64. More particularly, the flange 44 snaps in place between the protuberances 90 and the locating members 64, with nub 53 on flange 44 mating with the protuberances 90. The arm 46 on the left side of the tubular body 28 is held in place between locating members 64.

The hexagonal hole fixture 66 includes a hole 69 opening along the inner surface of the left housing section and a raised border 91 surrounding the hole 69. The hole 69 has a hexagonal configuration in cross-section to receive the end of the guide post 34 disposed at the lower left side of tubular body 28 with a snap or friction fit when the left housing section 18 is assembled on the hub 12. The left return wire 26B extending proximally from the flange 44 passes under and is guided by the left guide post 34 for passage through opening 60, and is thusly retained between the border 91 and the distal extension 41.

The detents 68 are similar to ratchet teeth and are arranged on the inner surface of the left housing section in an arcuate path to incrementally engage or lock the locking finger 62 as the handle 52 is depressed to rotate the lever 14 downwardly, i.e. clockwise looking at FIG. 1, toward the hub 12. The detents 68 are configured to cooperate with the forward edge of the locking finger to prevent rotation or pivotal movement of the handle 52 upwardly, counterclockwise looking at FIG. 1, from a downwardly rotated position. In this manner, the lever is locked in a selected pivoted position to hold the outer and inner members of the instrument at a desired angle or bend. The detents 68 are configured to cooperate with the rearward edge of the locking finger to facilitate movement of the locking finger therepast as the handle is depressed.

Figures 32, 35:
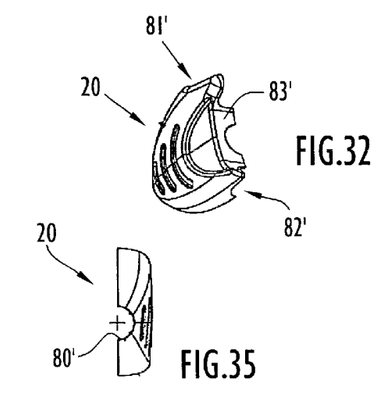
FIG. 32 is a rear perspective view of a right housing section of the housing for the articulating mechanism.
FIG. 35 is a front view of the right housing section.
Figure 33:
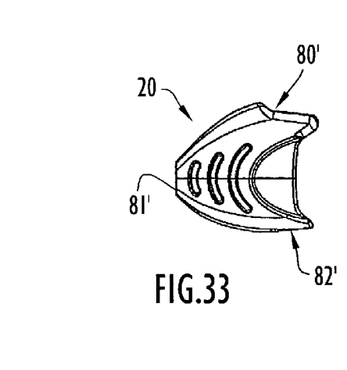
FIG. 33 is an exterior side view of the right housing section.
Figure 34:
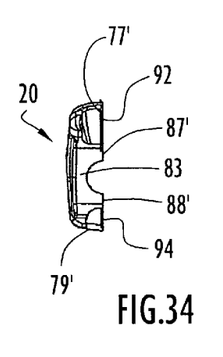
FIG. 34 is a rear view of the right housing section.
Figure 36:
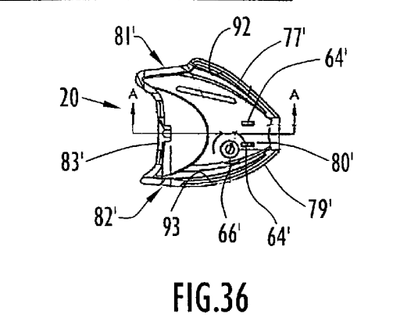
FIG. 36 is an interior side view of the right housing section.
Figure 37:
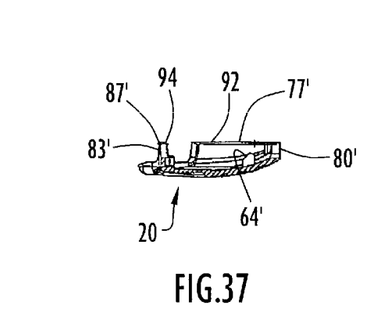
FIG. 37 is a cross-sectional view of the right housing section taken along line A—A in FIG. 36.
Figure 38:
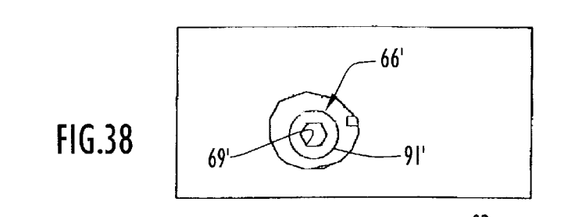
FIG. 38 is an enlarged fragmentary view of the interior of the right housing section.

FIG. 32 is a rear perspective view of the right housing section. FIG. 33 is a exterior side view of the right housing section. FIG. 34 is a rear view of the right housing section. FIG. 35 is a front view of the right housing section. FIG. 36 is an interior side view of the right housing section. FIG. 37 is a cross-sectional view of the right housing section taken through line A—A in FIG. 36. FIG. 38 is an enlarged fragmentary view of the interior of the right housing section illustrating the hexagonal hole fixture in detail.

As shown in FIGS. 32–38, right housing section 20 is similar to the left housing section but without one-way detents. The detents can, however, be formed on either or both housing sections. Also, the upper and lower edges 77' and 79', respectively, of the right housing section 20 are formed with upper and lower grooves 92 and 93, respectively, and the upper and lower edge segments 87' and 88', respectively, of the end wall 83' of right housing section 20 are formed with grooves 94. Accordingly, when the left and right housing sections 18 and 20 are assembled over the wire guide 16 and a distal portion of the tubular body 28, the upper and lower rims 84 and 85 along the upper and lower edges of the left housing section 18 are received in the upper and lower grooves 92 and 93, respectively, along the upper and lower edges of the right housing section 20. Also, the rims 89 disposed along the upper and lower edge segments of end wall 83 of left housing section 18 are received in the grooves 94 along the upper and lower edge segments of end wall 83' of right housing section 20. The guide post 34 along the lower right side of tubular body 28 engages in the hole 69' of the hexagonal hole fixture 66'. The right return wire 26A extending proximally from the flange 44 passes under and is guided by the right guide post 34 for passage through opening 60 and is thusly retained between the border 91' of the hexagonal hole fixture 66' and the distal extension 41. The arm 46 on the right side of the tubular body 28 is held in place between the locating members 64' of the right housing section. The upper notch 81' of the right housing section cooperates with the upper notch 81 of the left housing section to form a space through which the handle 52 extends from the housing in the proximal direction, such space being of sufficient size to accommodate pivotal movement of the handle. The lower notch 82' of the right housing section cooperates with the lower notch 82 of the left housing section to form a passage through which the irrigation port 30 extends proximally from the housing. The wire guide 16 extends through the distal or forward end of the housing with the distal edges 80 and 80' of the left and right housing sections forming a substantially continuous circular or circumferential edge around the external circumference of the cylindrical body 42 of wire guide 16, the continuous circumferential edge being aligned with or disposed slightly proximally of the junction 39. The recesses in end walls 83 and 83' cooperate to form an opening through which a proximal portion of the tubular body 28 extends proximally from the housing. The edge segments of end walls 83 and 83' defining the recesses, respectively, cooperate to form a substantially continuous circular or circumferential edge around the external circumference of the tubular body 28. The flange 78 is spaced proximally from the housing, which is disposed distally of a powered surgical handpiece to which the flange 78 and, therefore, the outer hub 12, is coupled.

Figure 39:
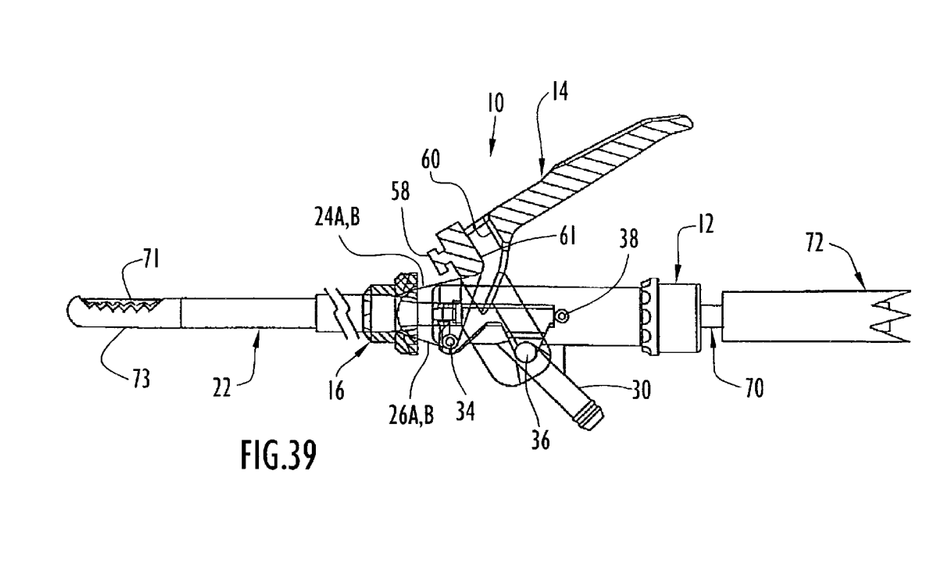
FIG. 39 is a broken side view, partly in section, of the articulating mechanism incorporated in a steerable surgical cutting instrument and showing the articulating mechanism in a rest position.
Figure 40:
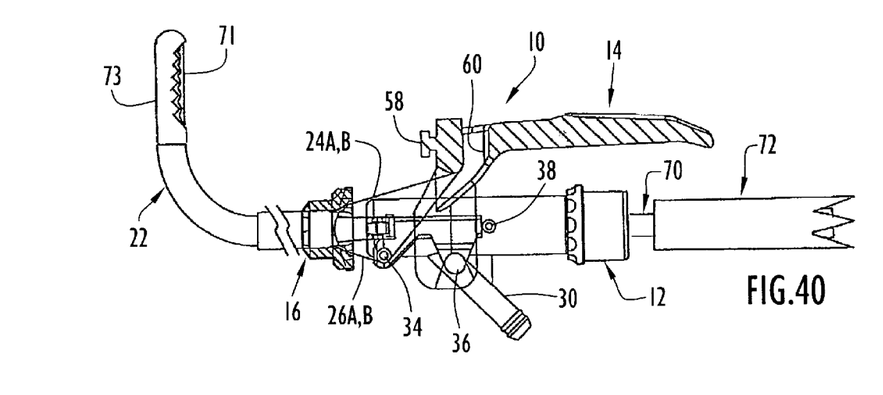
FIG. 40 is a broken side view, partly in section, of the steerable surgical cutting instrument showing the articulating mechanism in a fully actuated position.

FIGS. 39 and 40 illustrate the articulating mechanism incorporated in a steerable surgical cutting instrument and, in particular, a shaver of the type having inner and outer tubular members with apertured or open distal ends. It will be appreciated, however, that the inner member can have any type cutting tip including, but not limited to, cutting tips formed by apertures or burs. FIG. 39 is a side view, partly in section, of the articulating mechanism 10 in a rest position. FIG. 40 is a side view, partly in section, of the articulating mechanism 10 in a fully actuated or fully pivoted position.

In the assembled condition or state shown in FIGS. 39 and 40, wherein the housing is not shown for the sake of clarity, actuating wires 24A and 24B extend upwardly from flange 44 and under crosspiece 61 for upward passage through opening 60 in handle 52. Upon exiting the opening 60, the wires 24A and 24B pass over the top of crosspiece 61 and are attached at knob 58. The right actuating wire 24A passes over the top of crosspiece 61 to the right of button 63, and the left actuating wire 24B passes over the top of the crosspiece to the left of the button. Return wires 26A and 26B extend downwardly from flange 44 under guide posts 34 and upwardly through opening 60. The return wires pass over the top of crosspiece 61 and are attached to knob 58, with the right return wire 26A passing to the right of button 63 and the left return wire 26B passing to the left of the button. In use, an inner blade member 70 with a cutting tip 71 at a distal end thereof and an inner hub 72 secured to a proximal end thereof is inserted into the outer hub 12 and advanced distally through the outer tubular member or stem 22 until the cutting tip 71 is disposed adjacent or exposed from a cutting port or window at a distal end 73 of the outer member, with the inner hub disposed proximally of the outer hub. In FIGS. 39 and 40, the distal end of the outer member is formed with a cutting edge; however, the distal end of the outer member can be formed without a cutting edge. The inner and outer hubs 72 and are attached to a conventional powered handpiece, such as the STRAIGHTSHOT® handpiece made by Xomed Surgical Products of Jacksonville, Fla. and described in U.S. patent application Ser. Nos. 09/005,010, 09/005,014 and 09/005,189, filed on Jan. 9, 1998, the disclosures of which are incorporated herein by reference. Lever 14 of the articulating mechanism is located over the collet section of the handpiece when the outer hub 12 is mounted thereon. During operation, the handpiece rotates the inner blade member 70 within the stationary outer member 22 to cut tissue which is aspirated through the inner blade member. Irrigation fluid may be introduced through port 30 for passage between the outer and inner members and discharge through the open distal end 73. Lever 14 is used by the surgeon to control the degree of bend of the shaver blade during the surgical procedure, for example using the thumb or forefinger of a hand. With the lever in the rest position illustrated in FIG. 39, the actuating wires 24A and 24B are relaxed and the shaver blade is straight. When the surgeon desires to bend the tip of the shaver blade, lever 14 is pressed downwardly towards the handpiece, i.e. clockwise looking at FIG. 39, to cause the lever to pivot on the pins 36 extending from hub 12 to pull the actuating wires proximally and thus bend the tip. At the same time, return wires 26A and 26B are stretched super elastically. Locking member 62 on the lever rides over the detents 68 formed along the interior surface of left housing section 18 to provide passive position locking as the flexure angle is increased. The locking mechanism must be actively released for the flexure angle to be decreased, for example by rocking the lever away from the detents so that the locking member passes over the detents with some clearance. When the locking mechanism is released, the super elastic stretching of the return wires causes the lever to pivot upwardly away from the handpiece, i.e. counterclockwise looking at FIG. 40, such that the tip of the blade is returned to its original shape.

In an exemplary embodiment, the flexible portion of the outer member is an injection molded vertebrae with a length of flexure of about 0.720 inch and a range of motion of between 0° and 110° in a single plane. The actuating and return wires can be made of any suitable material, however, the return wires are preferably made of Nitinol. A powered shaver with an articulating mechanism according to the present invention is particularly useful in arthroscopic, spinal and ENT (ear, nose and throat) surgery.

The dimensions of the articulating mechanism can be varied in accordance with the instrument to be articulated.

Figure 41:
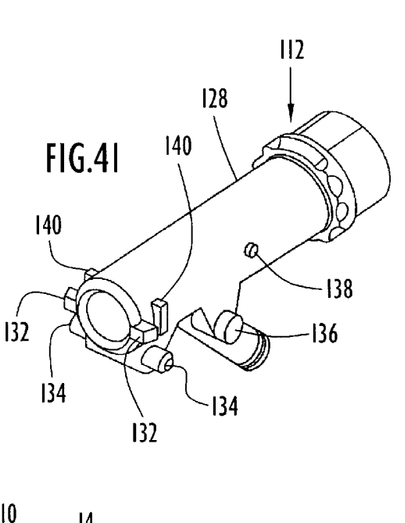
FIG. 41 is a perspective view of a preferred outer hub for the articulating mechanism.

FIG. 41 is a perspective view of a preferred hub 112 in which the hub 112 is made of plastic and the engagement members 132, the guide posts 134, the pivot pins 136, the first travel stop 138 and the second travel stops 140 are formed integrally, unitarily with the tubular body 128 of the hub 112.

Inasmuch as the present invention is subject to many variations, modifications, and changes in detail, it is intended that all subject matter discussed above or shown in the accompanying drawings be interpreted as illustrative only and not be taken in a limiting sense.

What is claimed is:

1. A steerable surgical cutting instrument for being powered by a powered surgical handpiece to cut anatomical tissue comprising
    a bendable outer tubular member having open distal and proximal ends;
    a bendable inner member disposed in said outer tubular member and having a distal end exposed from said distal end of said outer tubular member for cutting anatomical tissue and having a proximal end;
    at least one actuating wire extending proximally from said outer tubular member to effect bending of said outer and inner members when said actuating wire is pulled in a proximal direction;
    an inner hub secured to said proximal end of said inner member, said inner hub being releasably connectible with a powered surgical handpiece by which said inner member is rotated within said outer tubular member to cut anatomical tissue with said distal end of said inner member;
    an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub, said outer hub having a pair of opposed pivot pins disposed on opposite sides thereof, said pivot pins being disposed distally of the powered surgical handpiece when said outer hub is connected thereto; and
    an actuator pivotably mounted on said pivot pins, said at least one actuating wire being attached to said actuator, said actuator being selectively rotatable about said pivot pins in a first direction to pull said at least one actuating wire in said proximal direction to bend said outer and inner members.

2. A steerable surgical cutting instrument as recited in claim 1 wherein said at least one actuating wire extends proximally from a first side of said outer tubular member.

3. A steerable surgical cutting instrument as recited in claim 2 wherein said actuator includes a lever having a handle and a pair of pivot plates extending angularly from said handle, said pivot plates being spaced from one another to extend along said opposite sides, respectively, of said outer hub, said pivot plates having holes therein, respectively, for receiving said pivot pins.

4. A steerable surgical cutting instrument as recited in claim 3 wherein said actuator includes a retention member and an opening through which said at least one actuating wire extends from said outer tubular member for attachment to said retention member.

5. A steerable surgical cutting instrument as recited in claim 4 and further including a return wire extending proximally from a second side of said outer tubular member, opposite said first side, and through said opening, said return wire being attached to said retention member to effect straightening of said outer and inner members when said at least one actuating wire is not pulled in said proximal direction.

6. A steerable surgical cutting instrument as recited in claim 5 wherein said retention member includes a knob on said actuator around which said at least one actuating wire and said return wire are wrapped.

7. A steerable surgical cutting instrument as recited in claim 5 wherein said outer tubular member has an upper side corresponding to said first side and a lower side corresponding to said second side.

8. A steerable surgical cutting instrument as recited in claim 7 wherein said outer hub has left and right sides corresponding to said opposite sides, respectively.

9. A steerable surgical cutting instrument as recited in claim 3 and further including a first travel stop disposed on said outer hub proximally of said pivot pins to limit rotation of said actuator in said first direction.

10. A steerable surgical cutting instrument as recited in claim 1 wherein said distal end of said inner member is configured as a shaver.

11. A steerable surgical cutting instrument as recited in claim 1 wherein said pivot pins extend externally from said opposite sides, respectively.

12. A steerable surgical cutting instrument for being powered by a powered surgical handpiece to cut anatomical tissue comprising
    a bendable outer tubular member having open distal and proximal ends;
    a bendable inner member disposed in said outer tubular member and having a distal end exposed from said distal end of said outer tubular member for cutting anatomical tissue and having a proximal end;
    a pair of actuating wires extending proximally from an upper side of said outer tubular member to effect bending of said outer and inner members when said actuating wires are pulled in a proximal direction;
    an inner hub secured to said proximal end of said inner member, said inner hub being releasably connectible with a powered surgical handpiece by which said inner member is rotated within said outer tubular member to cut anatomical tissue with said distal end of said inner member;
    an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub, said outer hub having a pair of opposed pivot pins disposed on opposite sides thereof, said pivot pins being disposed on left and right sides, respectively, of said outer hub and being disposed distally of the powered surgical handpiece when said outer hub is connected thereto; and
    an actuator pivotably mounted on said pivot pins, said actuating wires being attached to said actuator, said actuator being selectively rotatable about said pivot pins in a first direction to pull said actuating wires in said proximal direction to bend said outer and inner members.

13. A steerable surgical cutting instrument for being powered by a powered surgical handpiece to cut anatomical tissue comprising
    a bendable outer tubular member having open distal and proximal ends;
    a bendable inner member disposed in said outer tubular member and having a distal end exposed from said distal end of said outer tubular member for cutting anatomical tissue and having a proximal end;

at least one actuating wire extending proximally from a first side of said outer tubular member to effect bending of said outer and inner members when said actuating wire is pulled in a proximal direction;

an inner hub secured to said proximal end of said inner member, said inner hub being releasably connectible with a powered surgical handpiece by which said inner member is rotated within said outer tubular member to cut anatomical tissue with said distal end of said inner member;

an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub, said outer hub having a pair of opposed pivot pins disposed on opposite sides thereof, said pivot pins being disposed distally of the powered surgical handpiece when said outer hub is connected thereto;

an actuator pivotably mounted on said pivot pins, said actuator including a lever having a handle and a pair of pivot plates extending angularly from said handle, said pivot plates being spaced from one another to extend along said opposite sides, respectively, of said outer hub, said pivot plates having holes therein, respectively, for receiving said pivot pins, said actuator including a retention member and an opening through which said at least one actuating wire extends from said outer tubular member for attachment to said retention member, said actuator being selectively rotatable about said pivot pins in a first direction to pull said at least one actuating wire in said proximal direction to bend said outer and inner members;

a return wire extending proximally from a second side of said outer tubular member, opposite said first side, and through said opening, said return wire being attached to said retention member to effect straightening of said outer and inner members when said at least one actuating wire is not pulled in said proximal direction, said return wire including a pair of return wires; and a pair of guide posts disposed on said opposite sides, respectively, of said outer hub distally of said pivot pins, said return wires extending from said outer tubular member and under said guide posts, respectively, prior to extending through said opening.

14. A steerable surgical cutting instrument for being powered by a powered surgical handpiece to cut anatomical tissue comprising a bendable outer tubular member having open distal and proximal ends;

a bendable inner member disposed in said outer tubular member and having a distal end exposed from said distal end of said outer tubular member for cutting anatomical tissue and having a proximal end;

at least one actuating wire extending proximally from a first side of said outer tubular member to effect bending of said outer and inner members when said actuating wire is pulled in a proximal direction;

an inner hub secured to said proximal end of said inner member, said inner hub being releasably connectible with a powered surgical handpiece by which said inner member is rotated within said outer tubular member to cut anatomical tissue with said distal end of said inner member;

an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub, said outer hub having a pair of opposed pivot pins disposed on opposite sides thereof, said pivot pins being disposed distally of the powered surgical handpiece when said outer hub is connected thereto;

an actuator pivotably mounted on said pivot pins, said actuator including a lever having a handle and a pair of pivot plates extending angularly from said handle, said pivot plates being spaced from one another to extend along said opposite sides, respectively, of said outer hub, said pivot plates haivng holes therein, respectively, for receiving said pivot pins, said at least one actuating wire being attached to said actuator, said actuator being selectively rotatable about said pivot pins in a first direction to pull said at least one actuating wire in said proximal direction to bend said outer and inner members;

a first travel stop disposed on said outer hub proximally of said pivot pins to limit rotation of said actuator in said first direction; and a pair of second travel stops disposed on said outer hub distally of said pivot pins to limit rotation of said actuator in a second direction opposite said first direction.

15. A steerable surgical cutting instrument for being powered by a powered surgical handpiece to cut anatomical tissue comprising a bendable outer tubular member having open distal and proximal ends and a lumen between said distal and proximal ends;

a bendable inner member disposed in said outer tubular member and having a distal end exposed from said distal end of said outer tubular member for cutting anatomical tissue and having a proximal end;

at least one actuating wire extending proximally from said outer tubular member to effect bending of said outer and inner members when said actuating wire is pulled in a proximal direction;

an inner hub secured to said proximal end of said inner member, said inner hub being releasably connectible with a powered surgical handpiece by which said inner member is rotated within said outer tubular member to cut anatomical tissue with said distal end of said inner member;

an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub, said outer hub having a pair of opposed pivot pins disposed on opposite sides thereof, said pivot pins being disposed distally of the powered surgical handpiece when said outer hub is connected thereto, said outer hub including an irrigation port communicating with said lumen of said outer tubular member; and an actuator pivotably mounted on said pivot pins, said at least one actuating wire being attached to said actuator, said actuator being selectively rotatable about said pivot pins in a first direction to pull said at least one actuating wire in said proximal direction to bend said outer and inner members.

16. A steerable surgical cutting instrument comprising a bendable outer tubular member having open distal and proximal ends;

a bendable inner member disposed in said outer tubular member and having a distal end exposed from said distal end of said outer tubular member for cutting anatomical tissue and having a proximal end;

at least one actuating wire extending proximally from one side of said outer tubular member to effect bending of said outer and inner members when said at least one actuating wire is pulled proximally;

at least one return wire extending proximally from an opposite side of said outer tubular member to effect straightening of said outer and inner members when said at least one actuating wire is not pulled proximally;

an inner hub secured to said proximal end of said inner member and being releasably connectible with a powered surgical handpiece by which said inner member is rotated within said outer tubular member to cut anatomical tissue with said distal end of said inner member;

an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub;

a wire guide disposed on said outer tubular member distally of said outer hub and having a lumen through which said at least one actuating wire and said at least one return wire extend proximally from said wire guide; and an actuator pivotably mounted on said outer hub and attached to said at least one actuating wire and said at least one return wire extending proximally from said wire guide, said actuator having a rest position wherein said outer and inner members are longitudinally straight, said actuator being selectively pivotable relative to said outer hub from said rest position to pull said at least one actuating wire proximally to bend said outer and inner members.

17. A steerable surgical cutting instrument as recited in claim 16 wherein said at least one return wire is adapted to effect automatic straightening of said outer and inner members when said at least one actuating wire is not pulled proximally.

18. A steerable surgical cutting instrument comprising a bendable outer tubular member having open distal and proximal ends;

a bendable inner member disposed in said outer tubular member and having a distal end exposed from said distal end of said outer tubular member for cutting anatomical tissue and having a proximal end;

at least one actuating wire extending proximally from one side of said outer tubular member to effect bending of said outer and inner members when said at least one actuating wire is pulled proximally;

at least one return wire extending proximally from an opposite side of said outer tubular member to effect straightening of said outer and inner members when said at least one actuating wire is not pulled proximally;

an inner hub secured to said proximal end of said inner member and being releasably connectible with a powered surgical handpiece by which said inner member is rotated within said outer tubular member to cut anatomical tissue with said distal end of said inner member;

an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub;

a wire guide disposed on said outer tubular member distally of said outer hub and having a lumen through which said at least one actuating wire and said at least one return wire extend proximally from said wire guide, said wire guide including a cylindrical body proximally joined to a flange and a pair of arms extending proximally from opposite sides of said flange, said lumen extending through said cylindrical body and said flange, a pair of openings disposed in said arms, respectively, and a pair of engagement members on said outer hub received in said openings, respectively; and an actuator pivotably mounted on said outer hub and attached to said at least one actuating wire and said at least one return wire extending proximally from said wire guide, said actuator having a rest position wherein said outer and inner members are longitudinally straight, said actuator being selectively pivotable relative to said outer hub from said rest position to pull said at least one actuating wire proximally to bend said outer and inner members.

19. A steerable surgical cutting instrument as recited in claim 18 wherein said wire guide includes an inner surface and a pair of opposed slots in said inner surface communicating with said lumen of said wire guide, one of said slots receiving said at least one actuating wire and the other of said slots receiving said at least one return wire.

20. A steerable surgical cutting instrument as recited in claim 19 wherein said at least one actuating wire includes a pair of actuating wires, said at least one return wire includes a pair of return wires, said actuating wires extend proximally from an upper side of said outer tubular member, said return wires extend proximally from a lower side of said outer tubular member, one of said arms extends along a left side of said outer tubular member and the other of said arms extends along a right side of said outer tubular member.

21. A steerable surgical cutting instrument as recited in claim 20 wherein one of said engagement members is disposed on a left side of said outer hub and the other of said engagement members is disposed on a right side of said outer hub.

22. A steerable surgical cutting instrument comprising
- a bendable outer tubular member having open distal and proximal ends;
- a bendable inner member disposed in said outer tubular member and having a distal end exposed from said distal end of said outer tubular member for cutting anatomical tissue and having a proximal end;
- at least one actuating wire extending proximally from one side of said outer tubular member to effect bending of said outer and inner members when said at least one actuating wire is pulled proximally;
- at least one return wire extending proximally from an opposite side of said outer tubular member to effect straightening of said outer and inner members when said at least one actuating wire is not pulled proximally;
- an inner hub secured to said proximal end of said inner member and being releasably connectible with a powered surgical handpiece by which said inner member is rotated within said outer tubular member to cut anatomical tissue with said distal end of said inner member;
- an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub;
- a wire guide disposed on said outer tubular member distally of said outer hub and through which said at least one actuating wire and said at least one return wire are guided to extend proximally of said wire guide;
- an actuator having a distal end pivotably mounted on said outer hub and secured to said at least one actuating wire and said at least one return wire extending proximally from said wire guide, said actuator having a rest position wherein said outer and inner members are longitudinally straight, said actuator being selectively pivotable relative to said outer hub from said rest position to a pivoted position to pull said at least one actuating wire proximally to bend said outer and inner members; and
- a pair of housing sections assembled over said wire guide and a distal portion of said outer hub to form a housing having a proximal end through which a proximal portion of said outer hub extends proximally from said housing.

23. A steerable surgical cutting instrument as recited in claim 22 wherein said actuator includes a locking member and one of said housing sections includes a plurality of detents for releasably lockingly engaging said locking member to lock said actuator in a plurality of incremental pivoted positions.

24. A steerable surgical cutting instrument as recited in claim 23 wherein said actuator includes a lever having a handle for being depressed to rotate said lever from said rest position to a pivoted position, said locking member is disposed on said handle, said one of said housing sections has an interior surface and said detents are disposed on said interior surface.

25. A steerable surgical cutting instrument as recited in claim 22 wherein said wire guide includes a cylindrical body proximally joined to a flange and said lumen extends through said cylindrical body and said flange, said cylindrical body has an external circumference and said housing sections have distal edges, respectively, cooperating to form a substantially continuous circumferential edge around said external circumference of said cylindrical body.

26. A steerable surgical cutting instrument as recited in claim 25 wherein said outer hub includes a tubular body having an external circumference and said housing sections have proximal edges, respectively, cooperating to form a substantially continuous circumferential edge around said external circumference of said tubular body.

27. A steerable surgical cutting instrument as recited in claim 26 wherein said housing sections have interior surfaces, respectively, protuberances along said interior surfaces, respectively, and locating members along said interior surfaces, respectively, spaced proximally from said protuberances, said flange being held between said protuberances and said locating members.

28. A steerable surgical cutting instrument as recited in claim 27 wherein said wire guide further includes a pair of arms extending proximally from opposite sides of said flange to ends having openings therein, said outer hub further includes a pair of engagement members on opposite sides of said tubular body received in said openings, respectively, and each of said housing sections includes a pair of said locating members between which one of said arms is retained.

29. A steerable surgical cutting instrument as recited in claim 22 wherein said outer hub includes a pair of guide posts disposed on opposite sides thereof, respectively, said housing sections have interior surfaces, respectively, and further including a pair of hole fixtures on said interior surfaces, respectively, receiving said guide posts, respectively, to secure said housing sections on said outer hub.

30. A steerable surgical cutting instrument as recited in claim 22 wherein said housing sections include upper and lower edges, said upper and lower edges of one of said housing sections have protruding rims, respectively, and said upper and lower edges of the other of said housing sections have grooves, respectively, receiving said protruding rims.

31. A steerable surgical cutting instrument as recited in claim 30 wherein said housing sections include notches proximally of said upper edges, respectively, cooperating to form a space through which said actuator extends from said housing, said space being of sufficient size to accommodate pivotal movement of said actuator from said rest position to said pivoted position.

32. A steerable surgical cutting instrument as recited in claim 31 wherein said outer tubular member has a lumen therethrough, said outer hub includes an irrigation port extending angularly therefrom and communicating with said lumen of said outer tubular member, said housing sections includes cut-outs along said lower edges, respectively, cooperating to form a passage through which said irrigation port extends from said housing.

33. A steerable surgical cutting instrument for being powered by a powered surgical handpiece to cut anatomical tissue comprising
- a bendable outer tubular member having open distal and proximal ends;
- a bendable inner member disposed in said outer tubular member and having a distal end exposed from said distal end of said outer tubular member for cutting anatomical tissue and having a proximal end;
- at least one actuating wire extending proximally from a first side of said outer tubular member to effect bending of said outer and inner members when said actuating wire is pulled in a proximal direction, said at least one actuating wire including a pair of actuating wires;

an inner hub secured to said proximal end of said inner member and being releasably connectible with a powered surgical handpiece by which said inner member is rotated within said outer tubular member to cut anatomical tissue with said distal end of said inner member;

an outer hub secured to said proximal end of said outer tubular member and being releasably connectible with the powered surgical handpiece to secure said outer tubular member while said inner member is rotated within said outer tubular member, said outer hub having a passage therethrough for receiving said inner member when said inner member is disposed in said outer tubular member with said inner hub disposed proximally of said outer hub, said outer hub having a pair of opposed pivot pins disposed on opposite sides thereof, said pivot pins being disposed distally of the powered surgical handpiece when said outer hub is connected thereto;

an actuator pivotably mounted on said pivot pins, said actuator including a lever having a handle and a pair of pivot plates extending angularly from said handle, said pivot plates being spaced from one another to extend along said opposite sides, respectively, of said outer hub, said pivot plates having holes therein, respectively, for receiving said pivot pins, said actuator including a retention member and an opening through which said at least one actuating wire extends from said outer tubular member for attachment to said retention member, said actuator being selectively rotatable about said pivot pins in a first direction to pull said at least one actuating wire in said proximal direction to bend said outer and inner members;

a return wire extending proximally from a second side of said outer tubular member, opposite said first side, and through said opening, said return wire being attached to said retention member to effect straightening of said outer and inner members when said at least one actuating wire is not pulled in said proximal direction, said return wire including a pair of return wires; and a pair of guide posts disposed on said opposite sides, respectively, of said outer hub distally of said pivot pins, said return wires extending from said outer tubular member and under said guide posts, respectively, prior to extending through said opening.

* * * * *